United States Patent [19]
Murray, Jr.

[11] Patent Number: 5,862,060
[45] Date of Patent: Jan. 19, 1999

[54] MAINTENANCE OF PROCESS CONTROL BY STATISTICAL ANALYSIS OF PRODUCT OPTICAL SPECTRUM

[75] Inventor: Richard C. Murray, Jr., Palatine, Ill.

[73] Assignee: UOP LLC, Des Plaines, Ill.

[21] Appl. No.: 755,425

[22] Filed: Nov. 22, 1996

[51] Int. Cl.⁶ ..................................................... G06F 19/00
[52] U.S. Cl. ................................ 364/528.01; 250/339.09
[58] Field of Search ..................................... 364/500, 496, 364/498, 550, 468.28, 554, 528.01, 528.06, 528.07; 356/300, 301, 302, 303; 250/339.12, 339.07, 339.09; 702/22, 23, 30, 31

[56] References Cited

U.S. PATENT DOCUMENTS

| | | | |
|---|---|---|---|
| 5,446,681 | 8/1995 | Gethner et al. | 364/554 |
| 5,658,423 | 8/1997 | Angell et al. | 364/468.28 X |
| 5,684,580 | 11/1997 | Cooper et al. | 356/301 |

*Primary Examiner*—Melanie Kemper
*Attorney, Agent, or Firm*—Thomas K. McBride; Frank S. Molinaro; Maryann Maas

[57] ABSTRACT

Control of many chemical processes is optimized using compositional data, rather than physical properties, as the means of control. Using near infrared spectroscopy as the analytical tool affords the opportunity for on-line measurements in real time. A calibration set of NIR spectra bounding the acceptable process space within which a particular property is to be controlled is obtained by conventional means. Applying a multivariant statistical method to the calibration set affords a method of identifying the most important characteristics of the set which governs the controlled property, and is inherently related to the composition of the process product. Control then is effected by using only a small number (2–4) of such characteristics, which can be determined quickly and simply from the measured spectra, as the control criteria to be applied to the process as a whole. The result is a very effective way of controlling a complex process using only 2–4 non-obvious criteria objectively determined from a calibration set and which can be applied in real time and virtually continuously resulting in a well-controlled process whose product composition is (ideally) invariant.

4 Claims, 4 Drawing Sheets

MAINTENANCE OF PROCESS CONTROL BY STATISTICAL ANALYSIS OF PRODUCT OPTICAL SPECTRUM

FIELD OF THE INVENTION

This invention relates to chemical process control. More particularly, the invention is directed toward controlling a chemical process by continuously monitoring the spectrum of a product over some subset of the electromagnetic spectrum, factoring the spectrum by a suitable statistical technique into a small number of discrete components or factors, and utilizing small differences between the factors observed and the factors of a "target" product to continuously adjust process variables so that the resulting product remains as similar as possible to the "target" product.

BACKGROUND OF THE INVENTION

The task of maintaining product quality in a chemical process is one of the basic tasks in the chemical and petroleum industries, and also has been the subject of continuing, intense scrutiny for many years now. Advances have been many and profound, beginning with occasional sampling of one or more products and attendant time-consuming analysis, comparison of the analytical data for the product with data for some "standard," and subsequent adjustment of the process according to empirical, often variable rules as an attempt to compensate for observed product changes. This approach had numerous failings. Sampling times were erratic and analyses often were time consuming, so that the analytical data were relevant to a process state far removed in time from that required. Relations between product differences and process variables were poorly understood and often were of limited corrective value, and different operators sometimes used quite different rules, so that product quality might vary depending upon the operator shifts. Interpretation of analytical results also was subjective, which together with the subjectivity of the effects of process variables on product could certainly lead to non-uniform process control not only at a particular site, but also among different reactors at a site, and certainly could lead to non-uniformity across different sites. Moreover, the samples removed from the process stream could undergo changes as a result of the change in environment (e.g., temperature, pressure, etc.) relative to the process stream.

In time, process control assumed increasing sophistication. In particular, analytical results were incorporated into a feedback loop, often at several points, so that variables could be changed at different points in the process. Analyses also could be taken of streams at different process points, and used either to control a process variable at a specified process point or to control several process variables concurrently, or analyses could be combined to control the variable at several process points. Analytical methods became increasingly sophisticated and, at least in simple cases, were effected in real time, so that the differential between times of obtaining raw data, of reducing the raw data to operationally meaningful data, and of using the latter for process control became more nearly contemporaneous. Finally, the digital revolution and customized or customizable microprocessors permitted controls to be effected extremely rapidly, to be applied to an extended number of process variables, and not only removed subjectivity but included the possibility of "learning on the fly" as the microprocessor and/or associated software gained "experience" in the control process, as, for example, using methods incorporating "artificial intelligence" into the control process. Note, however, that this latter advance was possible only when the necessary analytical data were available on a real-time basis.

This application focuses on spectroscopy as an analytical technique capable of giving truly real-time compositional data, albeit in a complex and non-intuitive form, and develops a particular means to use spectroscopic data in a control process. Emphasis is on spectroscopy because: 1) spectroscopic measurements can be performed continuously in situ and on-line, therefore data are real-time; 2) spectroscopic techniques are widely available; 3) unique and useful compositional information of any particular product is usually available from several regions of the electromagnetic spectrum; and 4) spectral data are amenable to some powerful statistical techniques to afford information especially valuable in control schemes. The following discussion will be couched in terms of near infrared spectroscopy (NIR), but we need to emphasize that our invention is applicable to optical spectroscopy generally, e.g., in the infrared, far infrared, ultraviolet, and visible regions of the electromagnetic spectrum and obtained using absorbance, fluorescence, emission, or Raman measurements. Consequently our use of NIR in the subsequent exposition is solely for clarity and simplicity of presentation, but is otherwise nonexclusive. In addition, the development of other real-time data sampling techniques in the near future will permit our approach to process control to be used equally well with analytical data from nuclear magnetic resonance spectroscopy, mass spectrometry, and fast gas chromatography.

SUMMARY OF THE INVENTION

Our invention is a method of effecting process control by statistical analysis of the optical spectrum of a product produced in a chemical process. An embodiment comprises measuring the optical spectrum of each member of a calibration sample set of selected products, determining by Principal Component Analysis or Partial Least Squares not more than four Factors to be used in the calibration sample set, determining the differences in Scores of the Factors between a standard "target" product and a test product, and using the differences to control at least one process variable so as to minimize said differences. In one embodiment the optical spectrum is the near infrared spectrum. Other embodiments will be evident from the description which follows.

DESCRIPTION OF THE INVENTION

Figure 1:
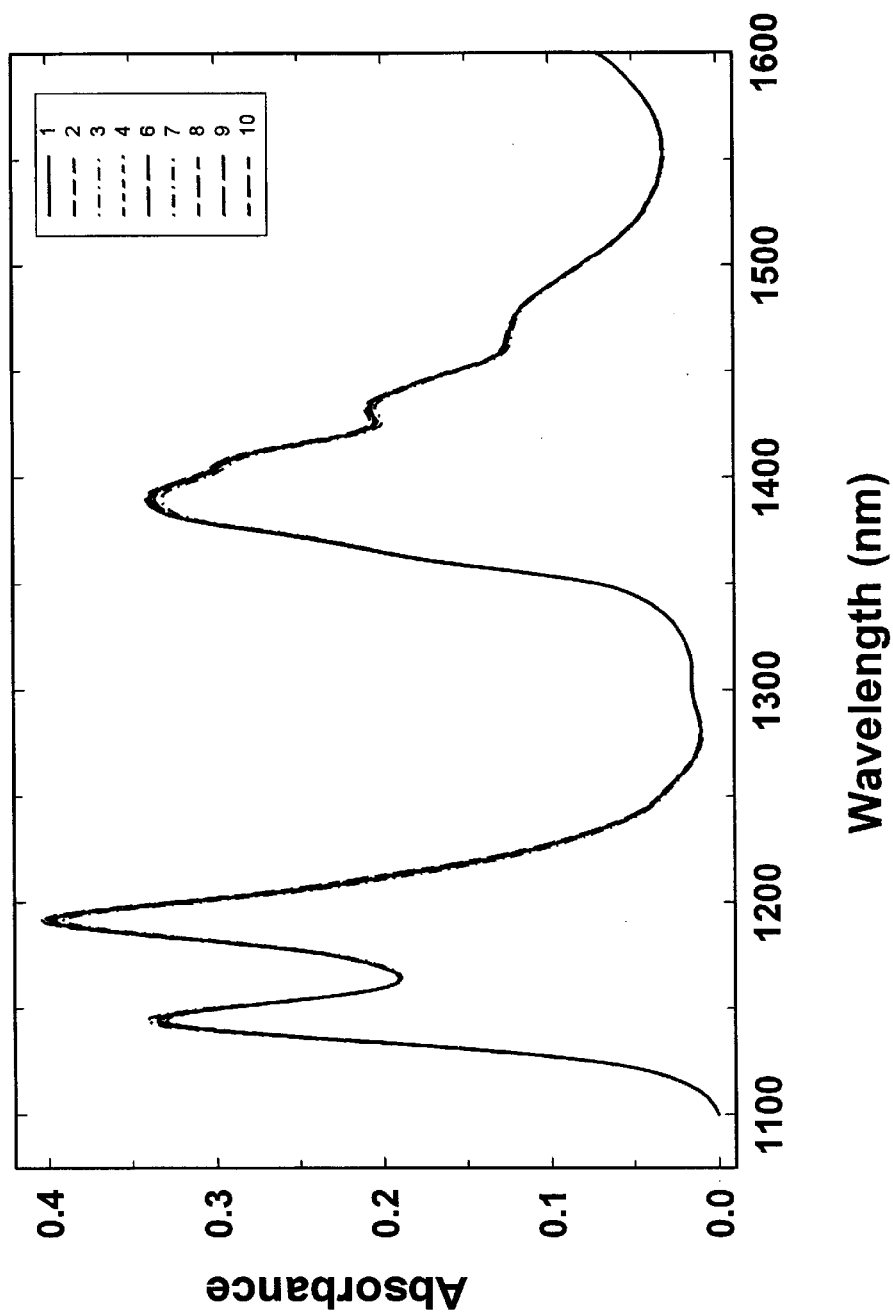
FIG. 1 shows the resulting NIR spectra of the reformate stream over a period of time.

This invention is applicable to any chemical process affording a stream whose quality may be said to define the "success" of the process and whose identity may be monitored by suitable spectroscopic means, especially NIR. The nature of the chemical process itself is not critical, nor is the specific identity of the stream whose spectrum is being obtained. What is critical is that an "ideal" or "target" stream can be defined, that its spectrum is known or can be determined, and that variations in the stream from the target can be controlled (i.e., reduced) using identifiable independent process variables, e.g., temperature, pressure, constituent concentrations, flow rates, etc. The ultimate goal of process control is to maintain a properly operating process at status quo. When a process has been deemed to have reached a proper operating condition, process control should be able to maintain it by proper adjustment of process parameters such as temperature, pressure, flow rate, residence time, and so forth. At proper operating conditions the process affords the "ideal" or "target" product stream.

The basic feature of our control process is that the spectrum of the stream, hereafter referred to as the test stream, is obtained continuously or in a near-continuous manner online, and compared to the spectrum of the "target" stream, hereafter referred to as the standard stream. The difference in the two spectra is then used to adjust one or more of the process variables so as to produce a test stream more nearly identical with the standard stream. However, as envisioned in practice, the complex spectral data will be reduced to no more than 4 numerical values which define the coordinates of the spectrum in the composition space of the process subject to control. Typically small, incremental adjustments will be made so that the test stream approaches the standard stream while minimizing oscillation, especially oscillations which will tend to lose process control rather than exercise control. Adjustments will be made according to one or more suitable algorithms based on process modeling, on process experience, or other means such as artificial intelligence feedback, as described more fully within. In principle more than one process variable may be subject to control, although it is apparent that as the number of process variables under control increases so does the complexity of the control process. Similarly, more than one test stream and more than one standard stream may be sampled either simultaneously or concurrently, again with an increase in complexity. (In its simplest form, where there is one test stream and one process variable under control, one may analogize the foregoing to the use of a thermocouple in a reactor to generate a voltage based on the sensed temperature, and to use the difference between the generated voltage and a setpoint voltage to send power to the reactor in proportion to the difference between the actual temperature and the desired temperature which, presumably, has been predetermined to be the optimum temperature.) Since the result of a given change in a process variable can be determined immediately, this new approach opens up the possibility of controlling the process by an automated "trial and error" feedback system, since unfavorable changes can be detected immediately. In essence, our invention operates as a null-detector with feedback from the set point of operation, where the feedback signal represents the deviation of the total composition of the stream from a target composition.

One difference between our invention and the prior art may be exemplified by process control in a reformer. The product is gasoline, and the characteristics of operational significance are the research octane number (RON), the benzene concentration, the Reid vapor pressure (RVP), and the paraffins, olefins, naphthenes, aromatics split (PONA). The group of RONs is not homomorphic to the other parameters of interest; i.e., gasoline of a particular RON does not have a unique PONA distribution but may have a rather broad range of PONAs. The same may be said of the relationship between RON and RVP, and so forth. Stated differently, there is not a 1-to-1 correspondence between a RON and a PONA. In the prior art, process control might have been effected by 1) obtaining the NIR spectrum or RVP of a test stream, 2) utilizing a correlation between NIR spectra of reformate streams and RON to calculate the RON of the test stream, 3) determining the difference between the calculated RON and the desired RON, and 4) using this difference to control, e.g., temperature in one portion of the reformer. However, we observed that when such a control process is utilized the product streams differ significantly in their PONA breakdown and benzene content even though their RONs may have been identical. Because PONA is an important quality index it is clear that the prior art method of control was faulty. Furthermore, with the implementation of reformulated gasoline regulations there is a need for controlling several of the foregoing parameters simultaneously, and this can most easily be accomplished by maintaining a target product (as opposed to attempting to readjust each variable individually and simultaneously to their target value).

Differences in composition between reformate having identical RONs are clearly demonstrated by gas-liquid chromatographic (glc) analyses, but glc analysis is time consuming and even though online analyses are possible these are not continuous and the results are complex and difficult to correlate when examined in detail. Consequently, the use of glc directly as the analytical method to generate process control presently is just not practical if one wishes tight, responsive quality control. On the other hand, the approach described here may be used with glc data (if obtained in real time) to reduce the complex chromatogram to a simpler numerical indication of deviations from the target. What we have observed is that the NIR spectra of reformate with identical RONs show small but unequivocal differences, and these differences, relative to an identifiable standard spectrum, contain sufficient information to permit simultaneous precise control over RON, PONA, and effectively every other parameter of the product (since the product itself will be identical).

Our method begins by taking NIR spectra of reformate of various grades and quality, spanning the maximum range of values of compositions (and hence RON and PONA) typical of the particular process. Such spectra then are representative of the entire range of reformates produced in this process; the collection of representative reformate streams itself is often referred to as calibration samples. Note that because the products (reformates) are representative of those formed in the process they constitute a subset of compositions which define the boundaries of representative products. It will be recognized that there is no subset which is unique; many different subsets may be used to define the boundaries, and the specific samples selected are not critical.

Subsequently, the spectra of the calibration samples are subjected to the well-known statistical technique of Principal Component Analysis, either directly or using Soft Independent Modeling of Class Analogy (SIMCA), to afford a small number of Principal Components (or Factors) which largely determine the spectrum of any sample. The Principal Components, which represent the major contributions to the spectral changes, are obtained from the reformate calibration samples by Principal Component Analysis (or SIMCA or Partial Least Squares). Thereafter, any new sample can be assigned various contributions of these Principal Components which would reproduce its spectrum. The amount of each Principal Component required is called its Score, and it is these Scores which are used to detect deviations from the "target" spectrum. In mathematical terms, for a set of spectra denoted by the matrix X, the use of Principal Component Analysis, for example, generates a set of Principal Component "loadings," P (which represent contributing spectral components) as eigenvectors of the equation $(X'X)P=PT$, and a Scores matrix, T, such that $X=TP'$. For the purposes of the process control envisioned in this application, only 2 or 3 Principal Components are needed to accommodate the data for a large range of reformates from a variety of plants. The spectrum of the standard sample is then expressed in terms of the Scores of the Principal Components used, the spectrum of the test sample is similarly expressed, and the difference in the Scores is used to control the process variables. Thus, no correlations between sample spectrum and RON or PONA need be known. In fact, the nature of the sample itself need not be known; what is important is that there be a standard, that the NIR spectrum of the standard be known, that a set of Principal Components be identified for the class of test stream samples, and that one can establish how to use the Principal Components to control the process variables (as discussed below).

The spectrum of any sample may be expressed as a 2-dimensional representation of the intensity of absorption at a particular wavelength vs. the wavelength. That is, one axis represents intensity, the other wavelength. The foregoing characterization of a spectrum is intended to incorporate various transformations which are mathematically covariant; e.g., instead of absorption one might use transmission, and either may be expressed as a percentage or logarithmically. Whatever the details, each spectrum may be viewed as a vector. The group of spectra arising from a group of samples similarly corresponds to a group of vectors. If the number of samples be n, there are at most n distinct spectra. If in fact none of the spectra can be expressed as a linear combination of the other spectra the set of spectra define an n-dimensional spectrum space. However, in the cases of interest here, where a particular stream in an invariant chemical process is being sampled it has been observed that in fact any particular spectrum can be accurately represented as a linear combination of a small number, m, of other spectra—their "principal components" which we refer to as "working" spectra. These "working" spectra may be viewed as the new basis set, i.e., linearly independent vectors which define the m-dimensional spectrum space in which the samples reside. The spectrum of any other sample is then of necessity a linear combination of the "working" spectra. Our experience demonstrates that the samples typically reside in, at most, a 4-dimensional spectrum space, and that a 2- or 3-dimensional model frequently suffices.

Statistical methods are available to determine the set of "working" spectra appropriate for any sample set, and the method of Principal Component Analysis (PCA) is the one most favored in the practice of our invention although other methods, e.g., partial least squares, SIMCA, (or, with less confidence, multiple linear regression), also can be utilized. The "working" spectra, or the linearly independent vectors defining the sample spectrum space, are called Principal Components or Factors. Thus the spectrum of any sample is a linear combination of the Factors. The fractional contribution of any Factor is called its Score. Hence, the spectrum of any sample completely defines a set of Scores which greatly reduces the apparent complexity of comparing different spectra. In fact, it has been found that for many processes of interest in petroleum refining a very small number of Factors, usually no more than 4, suffice to accurately define the sample spectrum space for the purpose of process control—and in some of these processes only 2–3 Factors need be used! This means that the process of characterizing the difference between a test sample and the standard sample comes down to the difference between 2–3 numbers—the Scores of the respective Factors for the sample and "target." It is significant to note that the small number of Scores embodies a great deal of information about the samples and the process, and the 2–3 numbers of importance are adequate to control the process within quite close tolerances. By using the null approach of our invention, the use of Scores is simplified to teaching small shifts (and restoring them to zero) rather than drawing conclusions or correlations from their absolute values.

Figure 2:
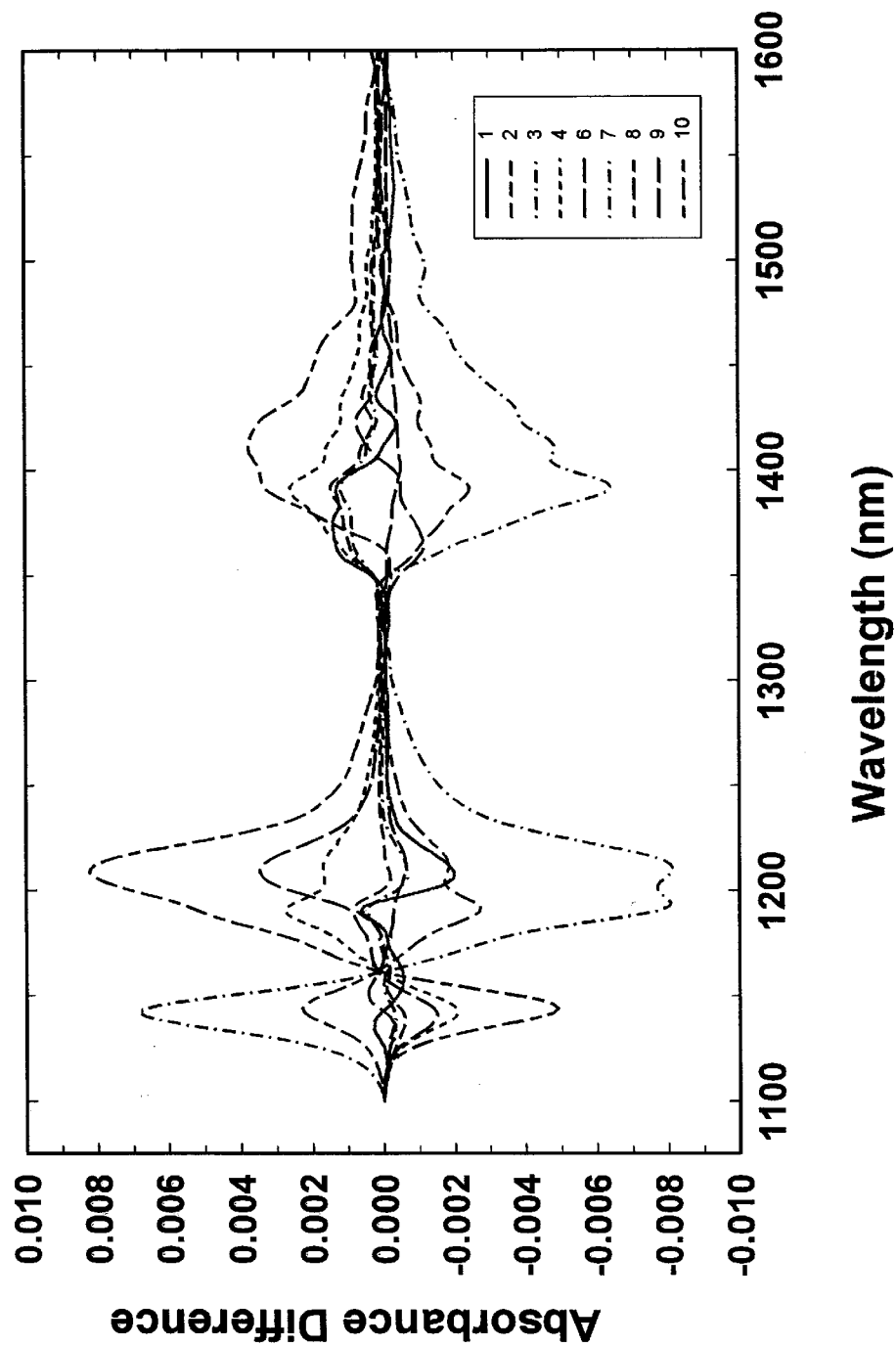
FIG. 2 shows difference spectra, i.e., the difference between the NIR spectrum of the reformate stream as measured and the "average" NIR spectrum of the sample group.

The foregoing approach may be illustrated by the following example which clearly shows the methodology and the comparison between traditional control methods and the approach herein. A reformate stream was the product whose RON was monitored in a traditional control process, and the process variables controlled were pressure, flow rates, and, in particular, bed temperatures at about 9 locations along the catalyst bed. The desired output was a reformate of fixed RON. The RON of the product was measured once or twice daily, using a knock engine following the method described in ASTM 2699, and deviations from the desired values were used as the basis for adjusting bed temperature to regain the desired RON. Higher temperatures produced higher RON. Although not used for control purposes, gas chromatographic data of the reformate were obtained for compositional information. The resulting NIR spectra of the reformate stream over a period of time is shown in composite in FIG. 1. Difference spectra, i.e., the difference between the NIR spectrum of the reformate stream as measured and the "average" NIR spectrum of the sample group, is shown in FIG. 2. Comparison of FIGS. 1 and 2 clearly show that whereas the raw NIR spectra appear almost identical, significant differences among the samples may be readily measured.

Figure 3:
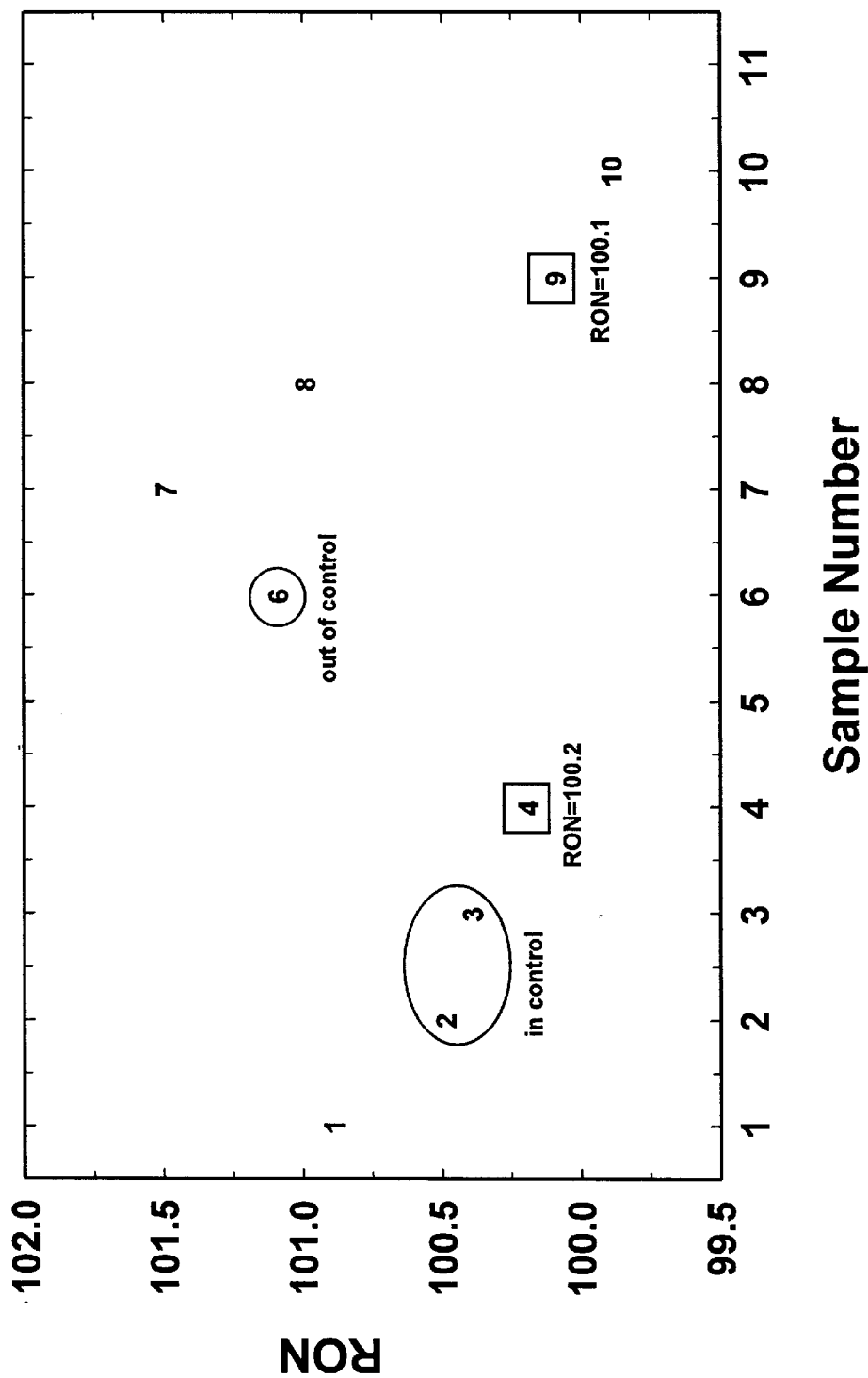
FIG. 3 shows RON data for the various samples.
Figure 4:
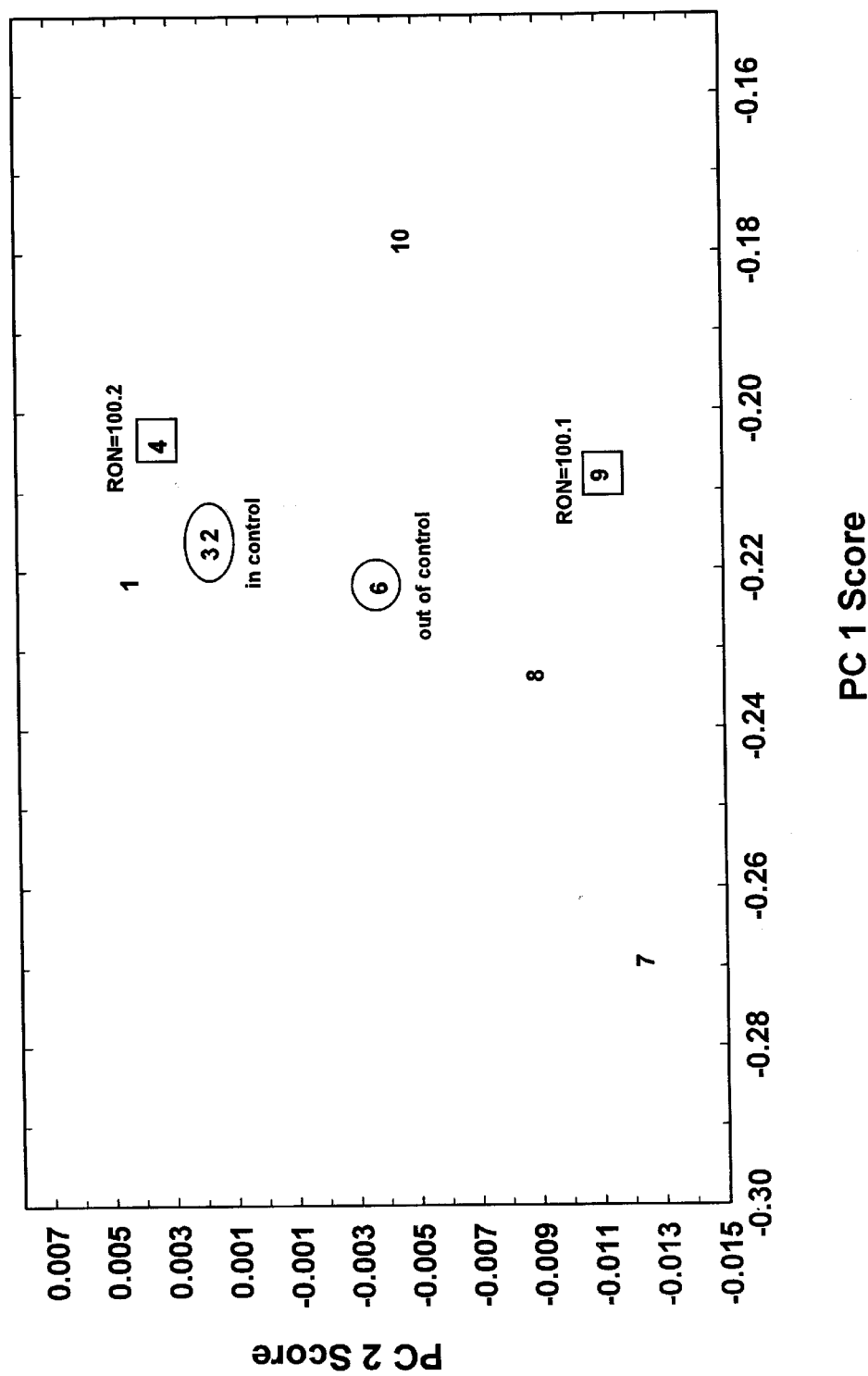
FIG. 4 shows a plot of the scores of Factor 1 vs. Factor 2 for the samples.

FIG. 3 shows RON data for the various samples, where the X-axis represents time periods and the numbers in the graph represent sample numbers. These data show that the RON remains within a narrow range, but with significant scatter within this range even though RON was the parameter being controlled. However, additional analytical data showed that although the RON remained within the desired range PONA did not, with considerable scatter in PONA values even for samples where the RON was virtually identical. In fact, these data showed that points 2 and 3 were the only samples within specifications for RON and PONA, and these samples represent the "in control" region. FIG. 4 presents data from a different perspective, and is a plot of the scores of Factor 1 vs. Factor 2 for the same samples. In particular, samples 2 and 3 represent the "in control" region and have comparable scores. Sample 6 is "out of control" since the combination of its RON and PONA values fall outside the specification; the figure clearly shows this arises through a variation in the score of just one of the factors. Perhaps even more interesting is the comparison between samples 4 and 9, which have virtually identical RON values but whose position in the scores plot varies enormously. As we expected, PONA analyses for these samples were significantly different.

Finally, Table 1 is an abridged table of the glc data of the samples of the previous figures. One conclusion to be gleaned from these data is that the relative lack of precision of the gic data relative to NIR data makes the latter an inherently more desirable control measurement. Secondly, even though on-line gic may be feasible, the measurement time is long relative to NIR, consequently there is a longer time lag between measurement and control; i.e., the control operation via glc measurement is to a process state further removed in time from the process state existing at measurement than that using NIR. Stated differently, there is more time for the process to have shifted further before control is effected when glc is used as the measured variable than when NIR is the measured variable.

The same reformer may be operated according to the method of this invention, where only the two Scores are used to control some combination of bed temperature, bed profile, pressure, and flow rate. One could expect that a process controlled by the Scores would show less variability in the product stream's NIR spectra. The gic data of the stream from the process controlled as described above also would unmistakably show much less scatter in the PONA distribution relative to the traditionally controlled reformate, and would demonstrate that the method of our invention does a far more effective job of maintaining constant chemical composition than the prior art method.

We envisage that the use of well known artificial intelligence techniques in the control process will have a significant impact on the process itself. In particular, the use of even simple artificial intelligence approaches will enable the nearly instantaneous feedback of the results of changes to process variables so that further corrections can be made in a more intelligent and more effective manner to restore the process to its target operating conditions.

TABLE 1

GLC Analysis of Reformate Samples

| Component | SAMPLE NUMBER | | | | | | | | |
|---|---|---|---|---|---|---|---|---|---|
| | 1 | 2 | 3 | 4 | 5 | 6 | 7 | 8 | 9 |
| RESEARCH OCTANE | 100.9 | 100.5 | 100.4 | 100.2 | 101.1 | 101.5 | 101.0 | 100.1 | 99.9 |
| TOTAL PARAFFINS | 29.0 | 28.6 | 28.5 | 28.4 | 27.5 | 25.8 | 26.4 | 27.4 | 30.7 |
| TOTAL OLEFINS | 2.0 | 2.1 | 2.1 | 2.3 | 2.5 | 2.5 | 2.9 | 3.1 | 0.0 |
| TOTAL NAPTHENES | 0.9 | 1.0 | 1.0 | 1.2 | 1.2 | 1.3 | 1.4 | 1.8 | 2.3 |
| TOTAL AROMATICS | 68.2 | 68.3 | 68.5 | 68.2 | 68.8 | 70.3 | 69.3 | 67.7 | 67.0 |
| BENZENE | 9.4 | 9.2 | 9.3 | 9.2 | 9.3 | 9.5 | 9.0 | 9.2 | 8.9 |
| TOLUENE | 27.7 | 28.0 | 28.1 | 27.5 | 28.3 | 29.2 | 28.8 | 28.0 | 27.9 |
| ETHYLBENZENE | 3.3 | 3.3 | 3.3 | 3.4 | 3.4 | 3.6 | 3.5 | 3.5 | 3.5 |
| P-XYLENE | 5.1 | 5.2 | 5.2 | 5.3 | 5.3 | 5.4 | 5.3 | 5.1 | 5.0 |
| M-XYLENE | 11.5 | 11.6 | 11.6 | 11.6 | 11.5 | 11.7 | 11.5 | 11.2 | 11.1 |
| O-XYLENE | 7.0 | 6.8 | 6.8 | 6.8 | 6.6 | 6.6 | 6.6 | 6.3 | 6.2 |
| C6 ISOPARAFFINS | 11.4 | 11.1 | 11.1 | 10.7 | 10.7 | 10.3 | 10.1 | 10.3 | 10.8 |
| METHYLCYCLOPENTANE | 0.2 | 0.3 | 0.3 | 0.4 | 0.5 | 0.5 | 0.5 | 0.6 | 1.0 |
| C7 ISOPARAFFINS | 6.0 | 5.9 | 6.0 | 6.1 | 5.5 | 4.7 | 5.2 | 5.3 | 6.0 |
| N-HEPTANE | 1.5 | 1.6 | 1.5 | 1.6 | 1.5 | 1.2 | 1.4 | 1.5 | 1.9 |
| 2,2-DIMETHYLBUTANE | 1.4 | 1.4 | 1.2 | 1.2 | 1.1 | 1.0 | 0.9 | 0.9 | 0.7 |
| 2,3-DIMETHYLBUTANE | 1.1 | 1.1 | 1.1 | 0.2 | 1.1 | 1.1 | 1.1 | 1.1 | 1.1 |
| 2-METHYLPENTANE | 5.2 | 4.9 | 5.1 | 5.3 | 4.8 | 4.7 | 4.7 | 4.8 | 5.2 |
| 3-METHYLPENTANE | 3.8 | 3.8 | 3.8 | 3.9 | 3.6 | 3.5 | 3.4 | 3.5 | 3.7 |

What is claimed is:

1. A method of controlling a chemical process comprising:
    a) obtaining the spectrum of each member in a set of calibration samples produced in said chemical process, said set of calibration samples being composed of members each of which are representative product streams of said chemical process, said set of calibration samples bounding a standard product stream of the chemical process;
    b) determining by principal component analysis a number, not more than four, of factors which can be used in combination with a score of that factor to express each spectrum in the calibration sample set;
    c) determining the scores of each factor for the absorption spectrum of the standard stream;
    d) determining the scores of each factor in the absorption spectrum of a test stream and determining their difference relative to the standard stream; and
    e) using the difference in the scores of each control the process.

2. The method of claim 1 where the spectrum is obtained in the optical range of the electromagnetic spectrum.

3. The method of claim 1 where the spectrum is a near infrared spectrum.

4. The method of claim 1 where the spectrum is a nuclear magnetic resonance spectrum.

* * * * *